(12) United States Patent
Cassella et al.

(10) Patent No.: US 12,133,915 B2
(45) Date of Patent: *Nov. 5, 2024

(54) METHOD OF TREATING EPILEPSY

(71) Applicant: ALEXZA PHARMACEUTICALS, INC., Mountain View, CA (US)

(72) Inventors: James Cassella, Essex, CT (US); Lily Gong, San Jose, CA (US); Edwin S. Kamemoto, Redwood City, CA (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/721,183

(22) Filed: Apr. 14, 2022

(65) Prior Publication Data

US 2022/0241191 A1 Aug. 4, 2022

Related U.S. Application Data

(63) Continuation of application No. 17/244,963, filed on Apr. 30, 2021, now Pat. No. 11,717,479, which is a continuation of application No. 16/469,143, filed as application No. PCT/US2017/065347 on Dec. 8, 2017, now Pat. No. 11,241,383.

(60) Provisional application No. 62/432,353, filed on Dec. 9, 2016, provisional application No. 62/485,281, filed on Apr. 13, 2017.

(51) Int. Cl.
*A61K 9/00* (2006.01)
*A61K 9/16* (2006.01)
*A61K 31/5517* (2006.01)
*A61P 25/08* (2006.01)

(52) U.S. Cl.
CPC .............. *A61K 9/0073* (2013.01); *A61K 9/16* (2013.01); *A61K 31/5517* (2013.01); *A61P 25/08* (2018.01)

(58) Field of Classification Search
CPC .... A61K 9/0073; A61K 9/16; A61K 31/5517; A61P 25/08
See application file for complete search history.

(56) References Cited

U.S. PATENT DOCUMENTS

| | | | |
|---|---|---|---|
| 6,682,716 B2 | 1/2004 | Hodges et al. | |
| 6,716,415 B2 | 4/2004 | Rabinowitz et al. | |
| 6,716,416 B2 | 4/2004 | Rabinowitz et al. | |
| 6,716,417 B2 | 4/2004 | Rabinowitz et al. | |
| 6,737,042 B2 | 5/2004 | Rabinowitz et al. | |
| 6,737,043 B2 | 5/2004 | Rabinowitz et al. | |
| 6,740,307 B2 | 5/2004 | Rabinowitz et al. | |

(Continued)

FOREIGN PATENT DOCUMENTS

| | | |
|---|---|---|
| CN | 110267662 A | 9/2019 |
| EP | 3551189 | 10/2019 |

(Continued)

OTHER PUBLICATIONS

Herink (Herink, J., "Effect of alprazolam and ketamine on seizures induced by two different convulsants," Acta Medica (Hradec Krazlove) 1997, 40(1), 9-11) (Year: 1997).*

(Continued)

*Primary Examiner* — Blessing M Fubara
(74) *Attorney, Agent, or Firm* — Quarles & Brady LLP

(57) ABSTRACT

Alprazolam formulated as an inhaled condensation aerosol and method for treating epilepsy and/or seizures.

34 Claims, 7 Drawing Sheets

(56) References Cited

U.S. PATENT DOCUMENTS

Figure 1:
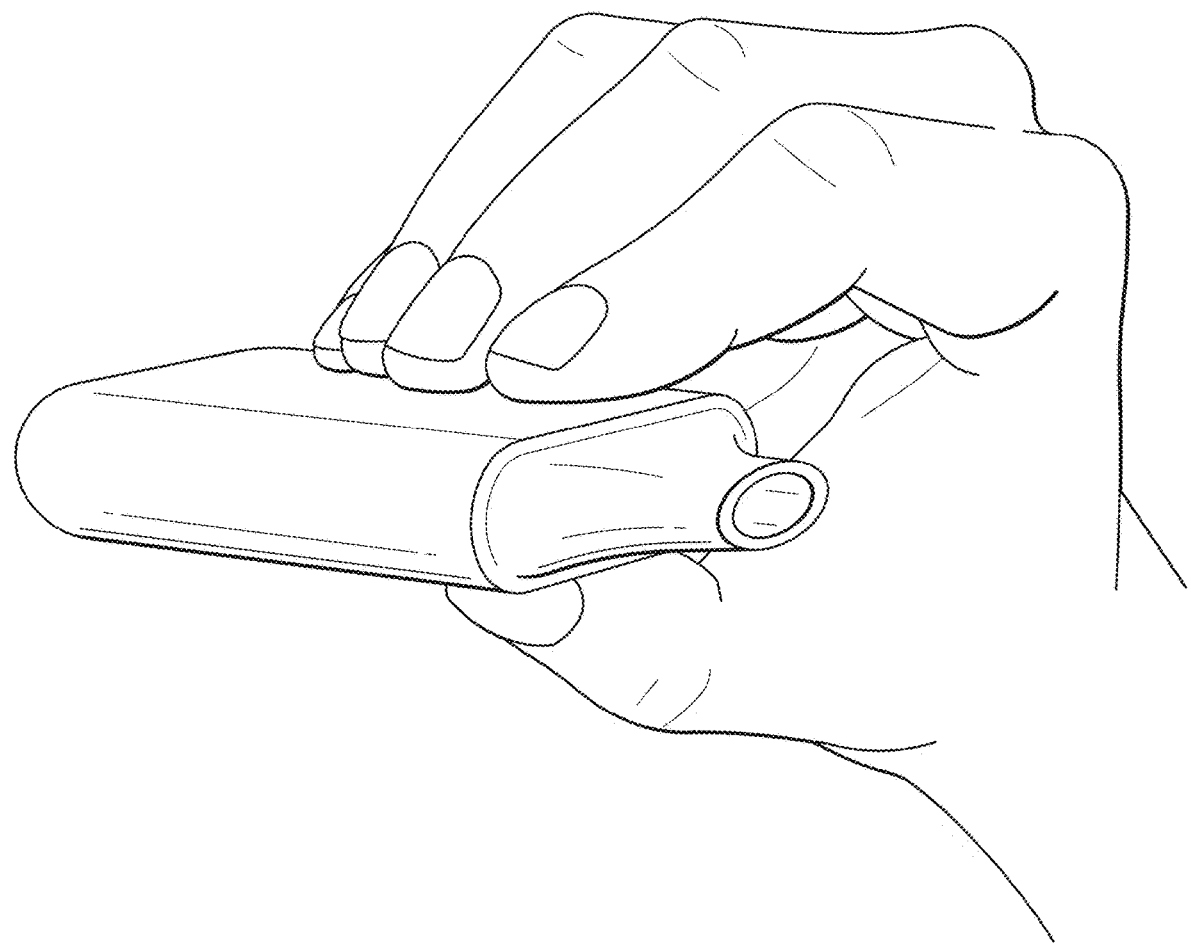

| Patent No. | Date | Inventor |
|---|---|---|
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,979,437 B2 | 12/2005 | Bartus et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Hale et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 * | 9/2009 | Hale ............... A61K 9/7007 128/200.14 |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 * | 8/2012 | Hale ............... A61K 9/0004 128/200.14 |
| 8,288,372 B2 | 10/2012 | Hale et al. |
| 8,333,197 B2 | 12/2012 | Cross et al. |
| 8,387,612 B2 | 3/2013 | Damani et al. |
| 8,506,935 B2 | 8/2013 | Hale et al. |
| 8,955,512 B2 | 2/2015 | Hales et al. |
| 8,991,387 B2 | 3/2015 | Damani et al. |
| 9,211,382 B2 | 12/2015 | Hale et al. |
| 9,439,907 B2 | 9/2016 | Hale et al. |
| 9,440,034 B2 | 9/2016 | Hale et al. |
| 9,687,487 B2 | 6/2017 | Hodges et al. |
| 9,724,341 B2 | 8/2017 | Myers et al. |
| 10,166,224 B2 | 1/2019 | Myers et al. |
| 10,350,157 B2 | 7/2019 | Hale et al. |
| 11,241,383 B2 * | 2/2022 | Cassella ............ A61P 25/08 |
| 11,511,054 B2 * | 11/2022 | Myers ............... A61P 25/20 |
| 2003/0032638 A1 | 2/2003 | Kim et al. |
| 2003/0051728 A1 | 3/2003 | Lloyd et al. |
| 2003/0118512 A1 | 6/2003 | Shen |
| 2003/0131843 A1 | 7/2003 | Lu |
| 2003/0138508 A1 | 7/2003 | Novack et al. |
| 2004/0096402 A1 | 5/2004 | Hodges et al. |
| 2004/0101481 A1 | 5/2004 | Hale et al. |
| 2004/0105818 A1 | 6/2004 | Every et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0121024 A1 | 6/2005 | Langford |
| 2005/0126562 A1 | 6/2005 | Rabinowitz et al. |
| 2005/0131739 A1 | 6/2005 | Rabinowitz et al. |
| 2005/0268911 A1 * | 12/2005 | Cross ............... A61M 11/002 128/203.26 |
| 2006/0032496 A1 | 2/2006 | Hale et al. |
| 2006/0120962 A1 | 6/2006 | Rabinowitz et al. |
| 2006/0193788 A1 | 8/2006 | Hale et al. |
| 2006/0257329 A1 | 11/2006 | Rabinowitz et al. |
| 2007/0122353 A1 | 5/2007 | Hale et al. |
| 2007/0286816 A1 | 12/2007 | Hale et al. |
| 2008/0038363 A1 | 2/2008 | Zaffaroni et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2009/0062254 A1 | 3/2009 | Hale et al. |
| 2009/0180968 A1 | 7/2009 | Hale et al. |
| 2010/0006092 A1 | 1/2010 | Hale et al. |
| 2010/0055048 A1 | 3/2010 | Hale et al. |

(56) References Cited

U.S. PATENT DOCUMENTS

| | | | |
|---|---|---|---|
| 2010/0065052 A1 | 3/2010 | Sharma et al. | |
| 2010/0068155 A1 | 3/2010 | Lei et al. | |
| 2010/0160240 A1 | 6/2010 | Gurd | |
| 2010/0181387 A1* | 7/2010 | Zaffaroni | A61M 11/042 239/128 |
| 2010/0294268 A1 | 11/2010 | Wensley et al. | |
| 2010/0300433 A1 | 12/2010 | Sharma et al. | |
| 2011/0233043 A1 | 9/2011 | Cross et al. | |
| 2011/0240013 A1 | 10/2011 | Hale et al. | |
| 2011/0240014 A1 | 10/2011 | Bennett et al. | |
| 2011/0240022 A1 | 10/2011 | Hodges et al. | |
| 2011/0244020 A1 | 10/2011 | Hale et al. | |
| 2011/0245493 A1 | 10/2011 | Rabinowitz et al. | |
| 2011/0253135 A1 | 10/2011 | Hale et al. | |
| 2012/0048963 A1 | 3/2012 | Sharma et al. | |
| 2013/0032139 A1 | 2/2013 | Hale et al. | |
| 2013/0156823 A1* | 6/2013 | Wu | A61P 25/22 424/45 |
| 2013/0180525 A1 | 7/2013 | Cross et al. | |
| 2013/0251813 A1 | 9/2013 | Cawello | |
| 2013/0287851 A1 | 10/2013 | Shaw | |
| 2014/0060525 A1 | 3/2014 | Hale et al. | |
| 2014/0060532 A1 | 3/2014 | Hodges et al. | |
| 2014/0066618 A1 | 3/2014 | Hale et al. | |
| 2014/0072605 A1 | 3/2014 | Bennett et al. | |
| 2015/0065491 A1 | 3/2015 | Cartt | |
| 2015/0157635 A1 | 6/2015 | Hale et al. | |
| 2015/0250800 A1 | 9/2015 | Hale et al. | |
| 2015/0265783 A1 | 9/2015 | Damani et al. | |
| 2016/0166564 A1 | 6/2016 | Myers et al. | |
| 2016/0324845 A1 | 11/2016 | Myers et al. | |
| 2016/0374937 A1 | 12/2016 | Hale et al. | |
| 2017/0049974 A1 | 2/2017 | Wensley et al. | |
| 2017/0105246 A1 | 4/2017 | Cross et al. | |
| 2017/0281884 A1 | 10/2017 | Hodges et al. | |
| 2018/0021328 A1 | 1/2018 | Myers et al. | |
| 2018/0126098 A1 | 5/2018 | Sharma et al. | |
| 2018/0296568 A1 | 10/2018 | Bennett et al. | |
| 2019/0021987 A1 | 1/2019 | Sharma et al. | |
| 2019/0117909 A1 | 4/2019 | Myers et al. | |
| 2019/0209546 A1 | 7/2019 | Myers et al. | |
| 2019/0307680 A1 | 10/2019 | Cassella et al. | |
| 2019/0336437 A1 | 11/2019 | Hale et al. | |
| 2021/0244661 A1 | 8/2021 | Cassella | |

FOREIGN PATENT DOCUMENTS

| | | |
|---|---|---|
| JP | 2004-531555 | 10/2004 |
| JP | 2005-530765 | 10/2005 |
| JP | 2008-530134 | 8/2008 |
| JP | 2012-180378 | 9/2012 |
| JP | 2020-500911 | 1/2020 |
| MX | 2019-006745 | 10/2019 |
| WO | WO 2002/024158 | 3/2002 |
| WO | WO 2002/094218 | 11/2002 |
| WO | WO 2004/104490 | 12/2004 |
| WO | WO 2006/044421 | 4/2006 |
| WO | WO 2006/088894 | 8/2006 |
| WO | WO 2008/137960 | 11/2008 |
| WO | WO 2012/075286 | 6/2012 |
| WO | WO 2013/096560 | 6/2013 |
| WO | WO 2018/107045 | 6/2018 |

OTHER PUBLICATIONS

Haut et al. (Haut et al., "Benzodiazepine use in seizure emergencies: A systematic review," Epilepsy & Behavior, 63 (2016), 109-117) (available online Sep. 6, 2016) (Year: 2016).*
U.S. Appl. No. 13/311,660, filed Dec. 6, 2011, Bennett et al.
U.S. Appl. No. 13/597,865, filed Aug. 29, 2012, Bennett et al.
Alexza Pharmaceuticals (2015) "AZ-002 (Staccato alprazolam) in epilepsy patients", Dec. 21, 2015, p. 1-6.
Boggs, J. G.(2004) "Mortality Associated with Status Epilepticus", Epilepsy Currents, vol. 4, No. 1, pp. 25-27.
Chen, Fuxin; "Nine types of drugs do not stop suddenly"; Beneficial Open Book—Asking for a Doctor and Asking for Medicine; Sep. 30, 2015; vol. 9, pp. 16-17 (w/ English Abstract).
Cleveland Clinic (2010) Article on types and symptoms of epileptic seizure, Dec. 30, 2010.
Communication pursuant to Article 94(3) EPC from European App No. 17878604.2, dated Apr. 15, 2021, 7 pages.
Dugan et al. (2015) Epilepsy Currents 15:75-77 "Auras Are Frequent in Patients with Generalized Epilepsy".
Extended European Search Report for Application No. 17878604.2, dated Jun. 22, 2020, 10 pages.
French et al. (2015) Epilepsy and Behavior 46:34-50 "The epilepsy foundation's 4th biennial epilepsy pipeline update conference".
Herink (1997) Acta Medica (Hradec Kralove), 40(1), 9-11 "Effect of alprazolam and ketamine on seizures induced by two different convulsants".
International Preliminary Report on Patentability for PCT/US2017/065347, dated Jun. 20, 2019, 6 pages.
International Search Report and Written Opinion for PCT/US17/65347, dated Feb. 22, 2018, 31 pages.
NS Healthcare (2014) (hllps://www.ns-healthcare.com/analysis/elegant-simplicity-single-dose-disposable-inhalers-4214657/) Jul. 4, 2014.
Office Action for Australia Application No. 2017370747, dated Apr. 29, 2020, 9 pages.
Office Action mailed Apr. 16, 2021 with respect to Australia App No. 2017370747, 5 pages.
Office Action from Canada Application No. 3,046,385, dated Jul. 8, 2020, 6 pages.
Office Action mailed Mar. 23, 2021 with respect to Canadian App No. 3,046,385, 6 pages.
Office Action mailed Dec. 20, 2021 with respect to Chinese Application No. 201780086216.6 (w/ English Translation), 12 pages.
Office Action from Japan App No. 2019-531043, dated Jun. 26, 2020 (w/English Translation) 12 pages.
Office Action mailed Feb. 2, 2021 with respect to Japanese App No. 2019-531043 (w/English Translation) 14 pages.
Office Action from New Zealand Application No. 754325, dated Jul. 27, 2020, 6 pages.
Office Action mailed Dec. 9, 2021 with respect to Korean App No. 10-2019-7019402 (w/English Translation), 12 pages.
Office Action mailed Jan. 28, 2022 with respect to Mexico App No. MX/a/2019/006745, 5 pages.
Office Action mailed Jan. 9, 2021 with respect to New Zealand App No. 754325, 6 pages.
Office Action mailed May 3, 2021 with respect to New Zealand App No. 754325, 4 pages.
Office Action mailed Aug. 2, 2021 with respect to New Zealand App No. 754325, 12 pages.
Porter (2017) Epilepsy Research 133: 110-112 "The photosensitivity model is not a model for partial (focal) seizures".
Rabinowitz et al. (2006) Journal of Pharmaceutical Sciences 95:2438-2451 "Ultra-Fast Absorption of Amorphous Pure Drug Aerosols Via Deep Lung Inhalation".
Stanton (2016) "Ferrer to add drug aerosol delivery tech through Alexza acquisition" Outsourcing Pharma, May 10, 2016, p. 1-2.
U.S. National Library of Medicine (2020) "Staccato Alprazolam and Photoparoxysmal Response", vol. 3, https://clinicaltrials.gov/ct2/show/NCT02351115, (retrieved on Nov. 11, 2020).
Valdes et al. (2014) P&T 39(9): 621-623, 648, "Loxapine Inhalation Powder (Adasuve) A New and Innovative Formulation of An Antiosvchotic Treatment for Adtation".
Alshehri et al. (2017) p. 875-883 Society for Academic Emergency Medicine "Intravenous Versus Nonintravenous Benzodiazepines for the Cessation of Seizures: A Systematic Review and Meta-analysis of Randomized Controlled Trials."
Altamura et al. (2013) "Understanding the pharmacokinetics of anxiolytic drugs" Expert Opinion on Drug Metabolism & Toxicology. 9:4, pp. 423-440.
Anderson, M. (2013) Patient Preference and Adherence 3(7):27-34 "Buccal midazolam for pediatric convulsive seizures: efficacy, safety, and patient acceptability".

(56) References Cited

OTHER PUBLICATIONS

Anonymous, (Jun. 1998) Guidance for Industry: Stability testing of drug substances and products, U.S. Department of Health and Human Services, FDA, CDER, CBER, pp. 1-110.
Anonymous (Sep. 2011) European Medicines Agency "EPAR summary for the public—Buccolam" pp. 1-3.
Asnis-Alibozek, et al, (2021) "The unmet need for rapid epileptic seizure termination (REST)", Epilepsy & Behavior Reports, vol. 15, p. 100409.
Communication pursuant to Article 94(3) EPC from European App No. 17878604.2, dated Jun. 29, 2022, 8 pages.
Examination Report 1 for Australia Application No. 2021202621, dated Jun. 27, 2022; 3 pages.
French J. et al, (2020) "A Two-Part, Phase 2b Efficacy Study of Staccato Alprazolam Inhaler in Patients with Epilepsy with a Predictable Seizure Pattern: Topline Results from Part 2", pp. 1-2.
Haidl et al. (2016) Respiratory Medicine 118:65-75 "Inhalation device requirements for patients' inhalation maneuvers."
Heyder, Joachim (2004) Proc. American Thoracic Soc. vol. 1:315-320 "Deposition of Inhaled Particles in the Human Respiratory Tract and Consequences for Regional Targeting in Respiratory Drug Delivery".
Lagae, Lieven (2014) Epileptic Disord. 16 (Suppl. 1): S44-S49 "Overview of clinical efficacy and risk data of benzodiazepines for prolonged seizures."
Lu, et al. (2008) "Photosensitivity in epileptic syndromes of childhood and adolescence", Epileptic Disord., vol. 10, No. 2, pp. 136-143.
Mula, Marco (2017) CNS Drugs 31:11-17 "New Non-Intravenous Routes for Benzodiazepines in Epilepsy: A Clinician Perspective".
Office Action mailed Oct. 22, 2021 with respect to Canadian App No. 3,046,385, 4 pages.
Office Action mailed Jun. 1, 2022 with respect to Chinese App No. 201780086216.6 (w/English Translation), 17 pages.
Office Action mailed Mar. 29, 2022 with respect to Japanese App No. 2021-093227 (w/English Translation), 5 pages.
Office Action mailed Nov. 1, 2022 with respect to Japanese App No. 2019-531043 (w/English Translation), 23 pages.
Office Action mailed Jul. 7, 2022 with respect to Korean App No. 10-2019-7019402 (w/English Translation), 14 pages.
Office Action mailed Oct. 5, 2022 with respect to U.S. Appl. No. 17/244,963.
Rey, et al. (1999) Clin Pharmacokinet. 36 (6):409-424 "Pharmacokinetic Optimisation of Benzodiazepine Therapy for Acute Seizures; Focus on Delivery Routes."
Talukdar et al. (2009) Brain & Development 31:744-749 "Efficacy of buccal midazolam compared to intravenous diazepam in controlling convulsions in children: A randomized controlled trial".
Trenite et al., (2016) "The 'Photosensitivity Model' is (also)a model for focal (partial) seizures", Epilepsy Research, Elsevier Science Publishers, Amsterdam, NL, vol. 133, pp. 113-120.
Arendt, et al. (1983) "In Vitro Correlates of Benzodiazepine Cerebrospinal Fluid Uptake, Pharmacodynamic Action and Peripheral Distribution", The Journal of Pharmacology and Experimental Therapeutics, vol. 227, No. 1, p. 98-106.
French J. et al. (2019) ""Inhaled alprazolam rapidly suppresses epileptic activity in photosensitive participants"", Epilepsia Online supplement. p. 1-6.
Maglalang, et al. (2018) "Rescue therapies for seizure emergencies: New modes of administration", Supplement Article, Epilepsia, 59(S2):207-215.
Office Action mailed Jan. 3, 2023 with respect to Chinese App No. 201780086216.6 (w/ English Translation), 17 pages.
Office Action mailed Nov. 22, 2021 with respect to Israel App No. 267199 (w English Summary) 9 pages.
Office Action mailed Aug. 13, 2021 with respect to Japanese App No. 2019-531043 (w/English Translation), 17 pages.
Office Action mailed May 25, 2021 with respect to Mexico App No. MX/a/2019/006745 (w/English Summary), 6 pages.
Office Action mailed Jun. 11, 2020 with respect to U.S. Appl. No. 16/469,143.
Office Action mailed Apr. 8, 2021 with respect to U.S. Appl. No. 16/469,143.
Shrewsbury, et al., "Breath-synchronized plume-control inhaler for pulmonary delivery of fluticasone propionate", International Journal of Pharmaceutics 356 (2008) 137-143.
Stapleton, K.W. "Orally inhaled migraine therapy: Where are we now?", Advanced Drug Delivery Reviews 133 (2018) 131-134.
Agarwal et al. (2015) "Development of benzodiazepines for out-of-hospital management of seizure emergencies", Neurology: Clinical Practice, Feb. 2015, pp. 80-86.
Ait-Daoud et al. (2018) "A Review of Alprazolam Use, Misuse, and Withdrawal", American Society of Addiction Medicine, vol. 12:1 pp. 4-10.
Brophy et al. (2012), "Guidelines for the Evaluation and Management of Status Epilepticus", Neurocrit Care (2012) 17:3-23, p. 1-23.
French et al. (2019) "Inhaled alprazolam rapidly suppresses epileptic activity in photosensitive participants", Epilepsia 00:1-8.
Glauser et al. (2016) "Evidence-Based Guideline: Treatment of Convulsive Status Epilepticus in Children and Adults: Report of the Guideline Committee of the American Epilepsy Society", Epilepsy Currents, vol. 16, No. 1, Jan./Feb. 2016, pp. 48-61.
Gommans et al. (2000) "Discriminative stimulus properties of alprazolam", Psychopharmacology 148:146-152.
Office Action mailed Nov. 3, 2022 with respect to Israel App. No. 267199 (w/ English Summary), 23 pages.
Office Action mailed Nov. 1, 2022 with respect to Japan App. No. 2019-531043 (w/ English Translation), 23 pages.
Office Action mailed Dec. 7, 2022 with respect to Korean App. No. 10-2019-7019402 (w/English Translation), 14 pages.
Verster et al. (2004) "Clinical Pharmacology, Clinical Efficacy, and Behavioral Toxicity of Alprazolam: A Review of the Literature", CNS Drug Reviews, vol. 10, No. 1, pp. 45-76.
Alexza Pharmaceuticals (2008) "Alexza Pharmaceuticals Announces Preliminary Results from its AZ-002 (Staccato® Alprazolam) Phase 2a Proof-of-Concept Trial in Patients with Panic Disorder" Jun. 9, 2008, p. 1-3.
Communication pursuant to Article 71(3) EPC from European App No. 17878604.2, dated May 3, 2023, 9 pages.
Communication pursuant to Article 71(3) EPC from European App No. 17878604.2, dated Jun. 2, 2023, 9 pages.
Manual of Clinical New Drugs and Special Drugs Manual, edited by Wang Lihua, Golden Shield Press, pp. 268, Alprazolam, published on Oct. 31, 2011 w English Translation.
Office Action mailed Jan. 12, 2023 with respect to Canadian App No. 3,046,385, 3 pages.
Office Action mailed Jan. 24, 2023 with respect to Japanese App No. 2021-093227, w/English Translation, 7 pages.
AES Poster (2020) "A two-part, phase IIb efficacy study of Staccato® alprazolam inhaler in patients with epilepsy with a predictable seizure pattern: topline results from part 2", Epilepsy Society (AES) 74th Annual Meeting, Dec. 2020.
Anonymous (2016) "Acorda to Discontinue Development of Plumiaz for Treatment of Epilepsy Seizure Clusters", Acorda Therapeutics. http://www.businesswire.com/news/home/20160520005142/en/.
Devinsky, et al. (2016) "Recognizing and preventing epilepsy-related mortality: A call for action", Neurology. 23;86(8):779-86.
Ellender et al, (2014) The Journal of Neuroscience, Nov. 12, 2014, 34(46):15208-15222, "Excitatory Effects of Parvalbumin-Expressing Interneurons Maintain Hippocampal Epileptiform Activity via Synchronous Afterdischarges".
Shorvon et al. (2008) "The drug treatment of status epilepticus in Europe: Consensus document from a workshop at the first London Colloquium on Status Epilepticus", Epilepsia. 2008; 49:1277-1288.

* cited by examiner

FIG. 2

Time = 0, Actuation of heating

Time = 30 ms

Time = 50 ms

Time = 200 ms

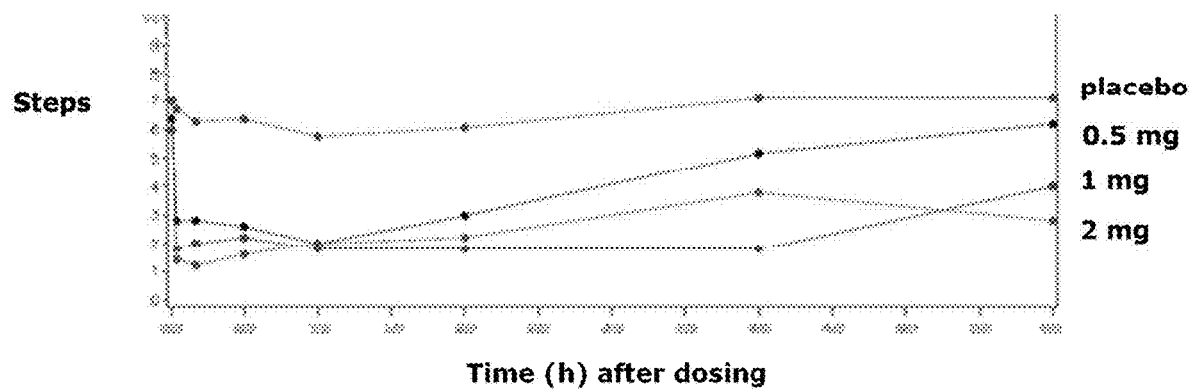
Fig. 6
 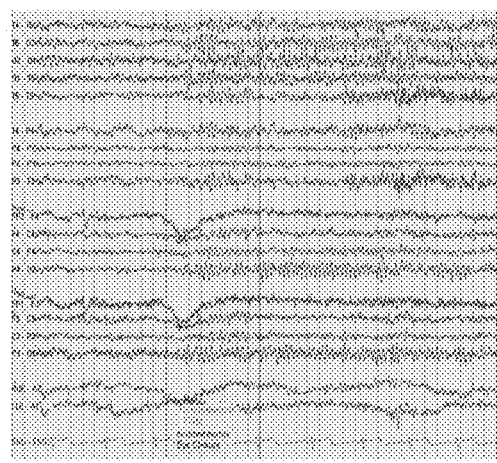
Fig. 7A                Fig. 7B

METHOD OF TREATING EPILEPSY

CROSS-REFERENCE TO RELATED APPLICATION

This application is a continuation of U.S. application Ser. No. 17/244,963 filed, Apr. 30, 2021, entitled "Method of Treating Epilepsy", which is a continuation of U.S. application Ser. No. 16/469,143, filed Jun. 12, 2019, now U.S. Pat. No. 11,241,383, entitled "Method of Treating Epilepsy", which application claims priority to and is a 35 U.S.C. § 371 national phase application of PCT/US2017/065347, filed on Dec. 8, 2017 entitled "Method of Treating Epilepsy", which application claims priority to U.S. provisional application Ser. No. 62/432,353, filed on Dec. 9, 2016 and 62/485,281, filed on Apr. 13, 2017. The entire disclosures of which are hereby incorporated by reference. Any disclaimer that may have occurred during the prosecution of the above-referenced applications is hereby expressly rescinded, and reconsideration of all relevant art is respectfully requested.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present invention relates generally to a method of treating epilepsy and/or seizure in a subject comprising administering to said subject in need thereof, a therapeutic dose of alprazolam via inhalation. More specifically, the invention relates to a method of treating epilepsy and/or seizure by administering a condensation alprazolam aerosol.

BACKGROUND

There are about three million patients with epilepsy in the U.S. There are two types of epileptic seizures: partial and generalized. Once diagnosed, patients are prescribed an anti-epileptic drug (AED). If two AEDs fail, the disease is considered refractory or uncontrolled. One million patients live with uncontrollable seizures because no available treatment works for them. About 200,000 or 20% of the uncontrolled population have a warning system, or a predictive pattern, alerting them to the onset of seizure activity. Warnings signals can occur minutes or days before and may include: muscle jerks, déjà vu, changes in behavior such as a "mean streak," visions or illusions, bad smells, anxiety, or flashing lights.

A seizure can be defined as abnormal, uncontrolled electrical activity in brain cells. Seizures can progress through four stages: prodrome, aura, ictal and post-ictal. The aura is a small partial seizure that is often followed by a larger event. Predictive patterns can occur during the prodrome and aura phases, which could allow those with such predictive patterns to be administered a drug to ameliorate or even abort seizure activity. To date, there are no out-of-office treatments indicated to treat seizures in these phases. The ictus or ictal phase is the main generalized seizure stage. What happens to the person during the seizure depends on where in the brain the disruption of neural activity occurs. Certain areas of the brain are more likely than others to be involved in seizure activity. The motor cortex, which is responsible for body movement, and the temporal lobes, including the hippocampus, which is involved in memory, are particularly sensitive to biochemical changes (e.g., decreased oxygen level, metabolic imbalances, infection) that provoke abnormal brain cell activity. Following a seizure, the person enters into the postictal state. Drowsiness and confusion are commonly experienced during this phase. The postictal state is the period in which the brain recovers from the insult it has experienced.

Episodes of repetitive seizures are distinct from their usual seizure pattern. Repetitive seizures comprise multiple seizures, such as 3 or more, within 24 hours in adults (12 hours in children). An episode may last from minutes to hours. These seizures are at a significantly higher risk for convulsive status epilepticus.

Benzodiazepines are seen as a treatment of choice for seizures. The drugs in this family have been observed as possessing sedative, tranquilizing and muscle relaxing properties. They are frequently classified as anxiolytic and skeletal muscle relaxants. They are thought to be useful in preventing, treating, or ameliorating the symptoms of anxiety, insomnia, agitation, seizures (such as those caused by epilepsy), muscle spasms and rigidity, the symptoms of drug withdrawal associated with the continuous abuse of central nervous system depressants, and exposure to nerve agents. Benzodiazepines are thought to act by binding to the $GABA_A$ receptor of a neuron, possibly causing the receptor to change shape and making it more accessible to gamma-aminobutyric acid (GABA).

Rectal diazepam (DZ) gel (Diastat®) is approved for treatment of acute repetitive seizures (ARS). It is administered only by a trained caregiver or healthcare professional and it takes multiple steps to administer the gel. It is likely to be used only for pediatric patients. Onset of therapeutic action is 30-40 minutes after administration, with 70-90% bioavailability of the administered dosage. The peak plasma concentration occurs at 1.5 hours after administration. Diazepam has a long half-life of 46 hours; Desmethyl-DZ, the active metabolite, has a half-life of 71 hours. Sedation and somnolence are known side effects.

Pharmaceutical compositions comprising one or more benzodiazepine drugs for nasal administration are disclosed in U.S. Pat. No. 8,895,546. Intranasal and intramuscular delivery of benzodiazepines such as midazolam or diazepam is not yet approved for treatment of ARS. It can take four steps to administer benzodiazepines intranasally. Onset of action can take 15-40 minutes, with only 40-80% bioavailability of the administered dosage. Side effects can include nasal irritation, amnesia, and blackbox respiratory depression.

Rectal, intranasal, and intramuscular administration of benzodiazepine drugs are administered in the post-ictal phase and address prevention of the next seizure, once the first seizure ends. It is desirable to identify and develop treatments that could be administered in the prodrome or aural stages of seizure activity to lessen the severity of, or even abort, the developing seizure. The present invention is directed toward overcoming or ameliorating one or more of the problems discussed above.

SUMMARY

The present invention provides methods for treating epilepsy and/or seizure in a mammal subject comprising administering a therapeutically effective dose of alprazolam via oral inhalation. The alprazolam is delivered in the form of an aerosol, e.g., condensation aerosol, through an oral inhalation route. In some embodiments, the patient is human.

The alprazolam aerosol contains particles of alprazolam having a particle size distribution. In one embodiment, at least 80% by weight of the alprazolam particles have a size less than 5 microns. In another embodiment, at least 90% by weight of the alprazolam particles have a size less than 5 microns. In another embodiment, at least 50% by weight of the alprazolam particles have a size less than 2 micron. In another embodiment, at least 50% by weight of the alprazolam aerosol particles have a size less than 1 micron. The alprazolam may be substantially excipient free, or excipient free in some embodiments.

The alprazolam dose administered to the subject exhibits unique $C_{max}$ and $T_{max}$ properties. For example, the alprazolam exhibits a plasma $T_{max}$ between from about 2 minutes to about 15 minutes post administration. In some embodiments, the $T_{max}$ is less than 15 minutes post administration, preferably less than 5 minutes post administration, or more preferably less than 2 minutes post administration. The $C_{max}$ is at least 5 ng/mL following oral administration. For example, the $C_{max}$ is at least 12 ng/mL following oral administration, or at least 30 ng/mL following oral administration.

The orally dosed alprazolam exhibits bioavailability that is similar to that of an intravenous administration. For example, the dosed alprazolam aerosol exhibits bioavailability from about 80-125% of that achieved with alprazolam administered intravenously.

The alprazolam may be self-administered at onset of one or more symptoms of an epileptic attack, or wherein the alprazolam is self-administered before onset of one or more symptoms of an epileptic attack, or wherein the alprazolam is self-administered after onset of one or more symptoms of an epileptic attack. The one or more symptoms of epilepsy include seizure; and/or wherein the treatment protects against seizure, reduces or ameliorates the intensity of seizure, reduces or ameliorates the frequency of seizure, interrupts the seizure cycle and/or prevents occurrence or re-occurrence of seizure.

Other embodiments include those wherein the seizure comprises an epileptic seizure, a breakthrough seizure, or other seizure; wherein the seizure comprises a partial (focal) or generalized seizure; such as those wherein the partial seizure comprises a complex partial seizure, simple partial seizure, or a seizure originating within neural networks limited to one brain hemisphere; or wherein the generalized seizure originates at some point within bilaterally distributed neural networks or evolves from a partial seizure.

The method also comprises administration of the alprazolam condensation aerosol when the subject is a patient in the prodrome or aura phase of seizure, such as when a patient is subjectively experiencing a sensory aura or an experiential aura, including wherein the sensory aura comprises a somatosensory, visual, auditory, olfactory, gustatory, epigastric or cephalic aura; or wherein the experiential aura comprises an affective, mnemonic, hallucinatory, or illusory aura. Another embodiment of the method is one wherein the subject is a patient with cluster or acute repetitive seizures, prolonged focal partial seizures, or juvenile myoclonic epilepsy.

The invention may be a rescue medication for the treatment of epilepsy and/or seizure. Upon actuation of the device described herein, the patient obtains a dose of alprazolam that provides immediate symptomatic relief.

The effect of the dosed alprazolam may be maximal within 2 to 15 minutes of inhalation of alprazolam. For example, the maximal effect may occur within 5 minutes of inhalation or within 2 minutes of inhalation of alprazolam.

Embodiments include those wherein epileptiform activity is absent within 15 minutes of inhalation of alprazolam; and/or wherein epileptiform activity is absent for at least six hours after inhalation of alprazolam.

Various modifications and additions can be made to the embodiments discussed without departing from the scope of the invention. For example, while the embodiments described above refer to particular features, the scope of this invention also includes embodiments having different combination of features and embodiments that do not include all of the above described features.

A further understanding of the nature and advantages of particular embodiments may be realized by reference to the remaining portions of the specification and the drawings, in which like reference numerals are used to refer to similar components.

BRIEF DESCRIPTION OF THE DRAWINGS

FIG. 1 shows a photograph of a device for the oral inhalation administration of alprazolam.

FIG. 2 shows cut-away schematic views of the device before and after inhalation initiates aerosol formation.

FIG. 3 shows photographs of aerosol generation at various time points after heating initiation in accordance with one embodiment of the invention.

FIG. 4 shows a graph of particle size distribution of alprazolam condensation aerosol emitted from a device in accordance with one embodiment of the invention.

FIGS. 5A and 5B show graphs of mean plasma concentration in phase 1 and phase 2a clinical trials respectively, in accordance with one embodiment of the invention.

FIG. 6 shows a graph of the mean standardized photosensitivity rage (SPR) over time in accordance with one embodiment of the invention.

FIGS. 7A and 7B show EEG traces of a representative patient prior to and after dosing with alprazolam condensation aerosol in accordance with one embodiment of the invention.

FIG. 8 shows a graph of the mean Visual Analogue Scale (VAS) for patients after dosing with alprazolam condensation aerosol in accordance with one embodiment of the invention.

DETAILED DESCRIPTION

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described and claimed herein, and while various features are ascribed to different embodiments, it should be appreciated that the features described with respect to one embodiment may be incorporated with other embodiments as well. By the same token, however, no single feature or features of any described or claimed embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." The modifier "about" is intended to have its regularly recognized meaning of approximately. In some embodiments, the term may be more precisely interpreted as meaning within a particular percentage of the modified value, e.g. "about" may in some embodiments mean±20%, ±10%, ±5%, ±2%, or ±1% or less.

In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

"Aerodynamic diameter" of a given particle refers to the diameter of a spherical droplet with a density of 1 g/mL (the density of water) that has the same settling velocity as the given particle.

"Aerosol" refers to a collection of solid or liquid particles suspended in a gas.

"Aerosol mass concentration" refers to the mass of particulate matter per unit volume of aerosol.

"Condensation aerosol" refers to an aerosol that has been formed by the vaporization of a composition and subsequent cooling of the vapor, such that the vapor condenses to form particles.

"Typical patient tidal volume" refers to 1 L for an adult patient and 15 mL/kg for a pediatric patient.

As used herein the phrase "therapeutically effective amount" (or more simply "effective amount") includes an amount sufficient to provide a specific therapeutic response for which the drug is administered to a patient in need of particular treatment. The therapeutic effect could be any therapeutic effect ranging from prevention, symptom amelioration, symptom treatment, to disease termination or cure. The skilled clinician will recognize that the therapeutically effective amount of drug will depend upon the patient, the indication and the particular drug administered.

As used herein, the term "seizure" includes commonly recognized types of seizures, including absence seizures, myoclonic seizures, clonic seizures, tonic seizures, tonic-clonic seizures, and atonic seizures.

As used herein, the term "prevention" refers to a forestalling, including temporary forestalling, of the onset of a disorder. In the case of seizures, this can occur either with or without the benefit of a warning aura.

The term "anticonvulsant" includes treatment of seizures, protection against seizure, reduction or amelioration of the intensity of seizure, reduction or amelioration of the frequency of seizure, and/or prevention of the occurrence or re-occurrence of seizure. In this regard, treatment of seizure includes cessation of an ongoing seizure, reduction in the severity of an ongoing seizure, or reduction in the duration of an ongoing seizure. Protection against seizure includes forestalling an oncoming seizure.

As used herein, the term "pharmacokinetics" (PK), refers to the chemical metabolism of a drug, its fate from the moment that it is administered up to the point at which it is completely eliminated from the body. Pharmacokinetics describes how the body affects a specific drug after administration through the mechanisms of absorption and distribution, metabolic changes of the substance in the body, and the effects and routes of excretion of the metabolites of the drug. Pharmacokinetic properties of chemicals are affected by the route of administration and the dose of administered drug. These may affect the absorption rate. "Pharmacodynamics" (PD), is the study of how the drug affects the organism, such as onset and duration of response to the drug. Both together influence dosing, benefit, and adverse effects, as seen in PK/PD models.

Alprazolam (API) is the international non-proprietary name for the compound 8-chloro-1-methyl-6-phenyl-4H-[1,2,4]triazolo [4,3-α][1,4]-benzodiazepine or 8-chloro-1-methyl-6-phenyl-4H-s-triazolo[4,3-α] [1,4]benzodiazepine (CAS Number 28981-97-7), molecular formula $C_{17}H_{13}ClN_4$. It is an odorless white, crystalline powder that is practically insoluble in water, soluble in ethanol and methanol, and freely soluble in chloroform. Its structure is shown as Formula I.

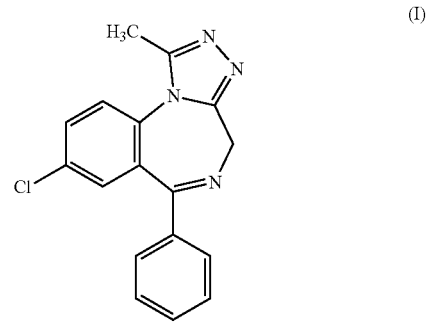 [SMILES: Cc1nnc2n1-c1ccc(Cl)cc1C(c1ccccc1)=NC2]

A brand name for alprazolam is Xanax®. Alprazolam may be manufactured using the process disclosed in U.S. Pat. No. 3,987,052. As used herein, the term "inhaled alprazolam" refers to a dose of alprazolam delivered by oral inhalation of a condensation aerosol from a device as described herein.

In one aspect, the invention provides methods for treating epilepsy and/or seizure in a mammal subject comprising administering a therapeutically effective dose of alprazolam. The alprazolam is delivered in the form of a condensation aerosol through an oral inhalation route. A therapeutically effective amount of alprazolam in some embodiments is from about 0.1 mg to about 2 mg. In some embodiments, the mammal is human.

The treatment of epilepsy and/or seizure includes protecting against seizure, reducing or ameliorating the intensity of seizure, reducing or ameliorating the frequency of seizure, interrupting the seizure cycle and/or preventing occurrence or re-occurrence of seizure. A particular embodiment is the method for acute treatment of seizures.

Epileptic patients can experience partial (focal) or generalized seizures. The current International League Against Epilepsy (ILAE) classification describes focal seizures as including seizures with or without impairment of consciousness and with specific autonomic, motor, psychic, sensory, or other phenomena. Focal seizures originate within neural networks limited to one brain hemisphere. A focal seizure can be consciousness (or awareness)-impaired (complex partial seizure), or be without impairment (simple partial seizure). Focal seizures can also evolve into a generalized seizure (focal to bilateral tonic-clonic). Generalized seizures originate at some point within, and rapidly engage bilaterally distributed neural networks.

The onset of both types of seizures can be preceded by an "aura" or a "warning". Often seizures, particularly severe tonic or tonic-clonic seizures, will be presaged by one or more aura events that will be familiar to the patient or to those familiar with the patient. An aura is defined as a subjective experience of a focal seizure that usually, or typically, precedes a patient's experiencing a seizure. These auras are practically sui generis for each patient. Each patient will generally experience a different type of aura that is unique to the patient. An aura can be classified as sensory (somatosensory, tactile, visual, auditory, olfactory, gustatory, epigastric or cephalic sensations) or experiential (affective, mnemonic, hallucinatory, or illusory). Not all patients who suffer seizures experience aura; however auras are not uncommon amongst those who suffer the worst type of seizures, especially tonic-clonic seizures.

In addition to subjects experiencing aura and/or secondarily generalized seizures, additional seizure events include cluster (acute repetitive) seizures, prolonged focal (partial) seizures, and juvenile myoclonic epilepsy.

The indication of "acute treatment of seizures" is directed to possible patient types in which rescue treatment with a rapid acting benzodiazepine such as alprazolam is warranted. It provides physicians the opportunity to identify their patients who can use and would most benefit from the rapid anti-epileptic activity.

Patients that can be treated with the invention include those who have a cluster of seizures or seizure events that include a predictable prodrome, aura, or evolution of their seizures, such that a change in that pattern of evolution can be detected. Examples of the latter are patients with aura, focal seizures that secondarily generalize, or patients with juvenile myoclonic epilepsy whereby the seizure typically manifests over a period of minutes.

Patients who can recognize aura as a precursor to a seizure would be candidates for self-administration. Patients with a focal seizure without impairment of consciousness/awareness would have the mental and motor capacity to be candidates for self-administration the invention. Patients with some impairment of awareness may be assisted by a caregiver for drug administration.

In addition to patients with aura and patients with secondarily generalized seizures, additional seizure events being considered include patients with cluster (acute repetitive) seizures, prolonged focal (partial) seizures, or juvenile myoclonic epilepsy. These patient types share the key characteristics of having the need for acute treatment but with the capacity for self-administration. In contrast, treatment of patients with status epilepticus would not be appropriate given that inhalation is required.

In some embodiments, the alprazolam condensation aerosol is administered by inhalation at any time before or after onset of symptoms of epilepsy and/or seizure. In some embodiments of the invention, the method includes prompt administration of a preparation of alprazolam according to the invention during the aura. In some embodiments, such inhalation administration of alprazolam, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Administration may occur when the subject is in the prodrome or aura phase of seizure. For example, the alprazolam may be administered when the subject experiences sensory aura, such as somatosensory, visual, auditory, olfactory, gustatory, epigastric or cephalic, experiential aura, such as affective, mnemonic, hallucinatory, or illusory auras.

The methods of the invention provide fast onset of therapeutic benefit. The present method may provide a rapidly effective rescue medication because in some instances the therapeutic effect is maximal within 15 minutes, or within 5 minutes, or within 2 minutes of inhalation of alprazolam. For example, epileptiform activity may be absent within 15 minutes, or within 5 minutes, or within 2 minutes of inhalation of alprazolam in accordance with the invention. Further, epileptiform activity may be absent for at least six hours after inhalation of alprazolam.

The alprazolam formulations of this invention also provide convenient administration of a therapeutically beneficial drug to a patient that does not require intravenous drug administration or rectal drug administration.

The method described herein can provide for improved bioavailability of alprazolam, delivery of higher concentrations of alprazolam via the oral inhalation route, faster attainment of therapeutic levels of alprazolam in the blood plasma, avoidance of the liver portal vein and concomitant avoidance of first pass effects and/or faster presentation of alprazolam to the brain. The method described and embodied herein achieves bioavailability that is from about 80-125% (e.g. about 90-110%, or more particularly about 92.5-107.5%) of that achieved with alprazolam administered intravenously. In some embodiments, the alprazolam and treatment with alprazolam are substantially non-irritating and well-tolerated.

In one embodiment, the loaded alprazolam is an inhalation powder supplied in a single-use, disposable inhaler for oral inhalation. Doses may range from 0.125 mg to 4 mg of alprazolam. In some embodiments, the therapeutic dose is in the range of about 0.5 to about 4, preferably about 1 to about 2 mg per dose, as needed to treat seizures. As aerosols, 0.5 mg to 4 mg, preferably 0.5 to 2 mg, alprazolam are generally provided per inspiration for the treatment of seizures. Dosages administered may be dependent on such factors as body weight, age and sensitivity to side effects of the patient to which the alprazolam is administered. Consideration of such factors may be used by a health care professional to determine the desired dosage for an individual.

In some cases, administration of alprazolam condensation aerosols may be up to eight times a day when a patient is experiencing seizure activity, such as from 1 to 8, or 2 to 8, or 1 to 4, or about 4 to about 6 times per day.

Alprazolam formulated as an inhaled preparation as described herein is a rapidly effective rescue medication for epilepsy patients. Time to effect is assessed in patients with photosensitive epilepsy, in whom epileptiform activity can be elicited at will. It has been found that inhaled alprazolam strongly suppresses epileptic activity within 2 minutes. Duration of effect was dose related, as was sedation. Inhaled alprazolam has utility in stopping a seizure within 2 minutes of use.

The condensation aerosols of the various embodiments may be formed by preparing a film containing a drug composition of a desired thickness on a heat-conductive and impermeable substrate and heating said substrate to vaporize said film, and cooling said vapor thereby producing aerosol particles containing said drug composition. Rapid heating in combination with the gas flow helps reduce the amount of decomposition. Thus, a heat source is used that typically heats the substrate to a temperature of greater than 200° C., preferably at least 250° C., more preferably at least 300° C.

or 350° C., or to 390° C.±50° C. and produces substantially complete volatilization (vaporization) of the drug composition from the substrate within a period of 2 seconds, preferably, within 1 second, and more preferably, within 0.5 seconds. Typically, the gas flow rate over the vaporizing compound is between about 4 and 50 L/minute. The heating of the alprazolam composition is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials. Heat sources or devices that contain a chemically reactive material which undergoes an exothermic reaction upon actuation, e.g., by a spark or heat element, such as flashbulb type heaters are also suitable. In particular, heat sources that generate heat by exothermic reaction, where the chemical "load" of the source is consumed in a period of between 50-500 msec or less are generally suitable, assuming good thermal coupling between the heat source and substrate.

The film thickness is such that an aerosol formed by vaporizing the compound by heating the substrate and condensing the vaporized compound contains 10% by weight or less of drug-degradation product(s). The use of thin films allows a more rapid rate of vaporization and hence, generally, less thermal drug degradation. Typically, the film has a thickness between 0.05 and 20 microns, such as between 0.1 and 10 microns. In some variations, the film has a thickness between 0.5 and 5 microns. The selected area of the substrate surface expanse is such as to yield an effective human therapeutic dose of the drug aerosol.

Figure 2:
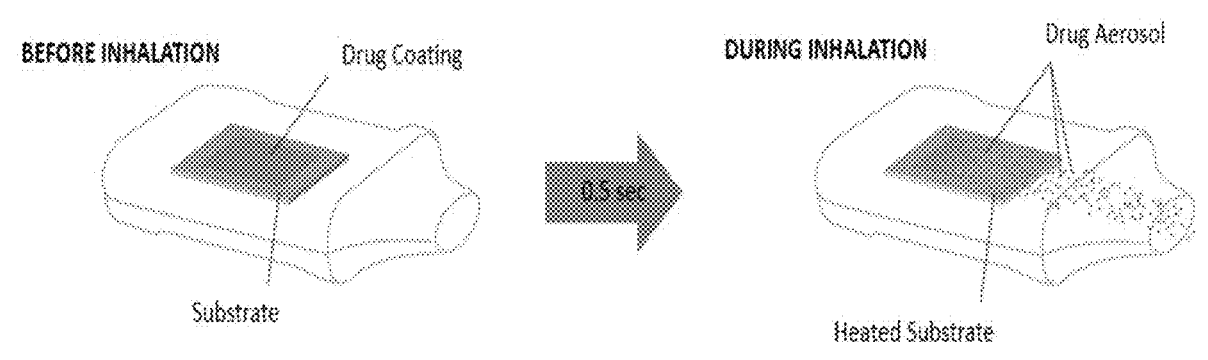

Alprazolam aerosols of the invention are delivered to a mammal using an inhalation device. A photograph of one embodiment of the inhalation device is shown in FIG. 1. The delivery device comprises an element for heating the composition to form a vapor and an element allowing the vapor to cool, thereby forming a condensation aerosol. Referring to FIG. 2 schematic cut-away views of the device are depicted before and after vaporization is initiated. The resultant aerosol from the vaporization is generally delivered via inhalation from the device to the lungs of a subject, for local or systemic treatment.

In one embodiment the aerosol is a condensation aerosol. With regard to the condensation aerosol, the delivery device as depicted in FIG. 1 and FIG. 2 includes a first element for heating an alprazolam composition to form a vapor; a second element allowing the vapor to cool, thereby providing a condensation aerosol; and, a third element permitting inhalation of the aerosol.

Various suitable first heating elements are described above, and involve a heatable substrate coated with a film of alprazolam. Typically, the substrate or support is heated to a temperature sufficient to vaporize all or a portion of the alprazolam film, so that the composition forms a vapor that becomes entrained in a stream of air during inhalation.

The second element that allows cooling is, in its simplest form, an inert passageway linking the heating element to the inhalation element. The third element permitting inhalation is an aerosol exit portal that defines a connection between the cooling element and the mammal's respiratory system, such as a mouthpiece.

Figure 3:
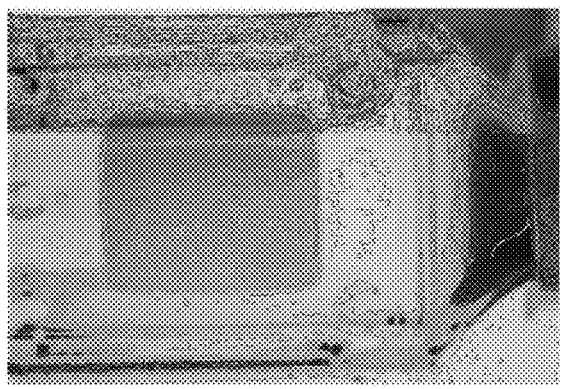
Figure 3:
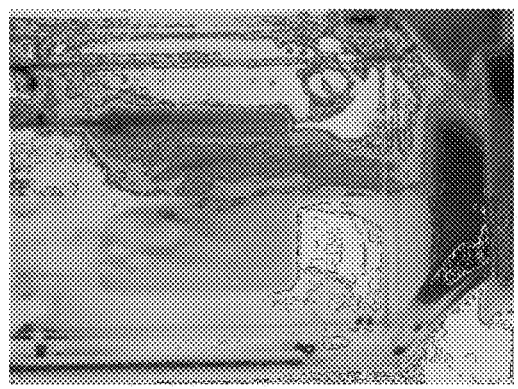
Figure 3:
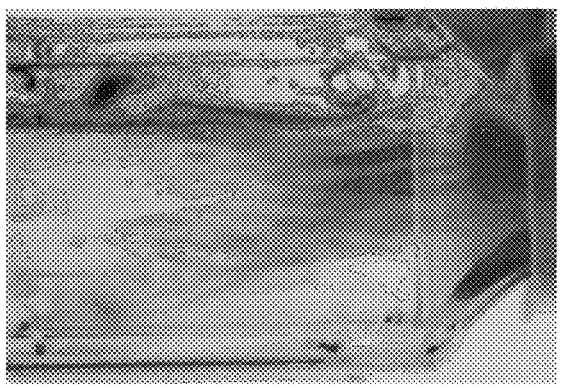
Figure 3:

FIG. 3 shows high speed photographs showing the generation of aerosol particles from a device similar to the device of FIG. 1. The device has a heat-conductive substrate about 2 cm in length coated with a film of drug. The drug-coated substrate was placed in a chamber through which a stream of air was flowing in an upstream-to-downstream direction (from left to right in FIG. 3) at rate of about 15 L/min. The substrate was electrically heated and the progression of drug vaporization monitored by real-time photography. The photographs show the sequence of drug vaporization and aerosol generation at time intervals of 30 milliseconds (msec), 50 msec, and 200 msec, respectively after initiation of heating (time=0). The white cloud of drug-aerosol particles formed from the drug vapor entrained in the flowing air is visible in the photographs. Complete vaporization of the drug film was achieved by 500 msec and the vapor can be seen exiting the device at the right.

Inhalation through the device is detected by the breath sensor, which generates an electrical signal that activates the starter to initiate the redox reaction. This leads to rapid heating of the exterior surface of the hermetically sealed heat package to approximately 390° C.±50° C., which is also accompanied by a clicking sound associated with the thermal expansion of the stainless steel. Heat then transfers into the alprazolam coated as a thin film on the heat package exterior. Because the thin film of alprazolam has a high surface area, vaporization of the alprazolam is very rapid, occurring in less than 1 second and before substantial thermal decomposition can occur.

The alprazolam aerosol of the invention has a mass median aerodynamic diameter (MMAD) of about 0.5 μm to 3.0 μm. The aerosol particle size diameter preferably is from 0.5 to 3 microns, which is optimal for deep lung delivery. The pharmacokinetics of the administered alprazolam dose is similar to an IV injection. Achievement of peak plasma levels within minutes via a simple, user-friendly delivery system makes the invention ideal for the acute treatment of seizures.

Figure 4:
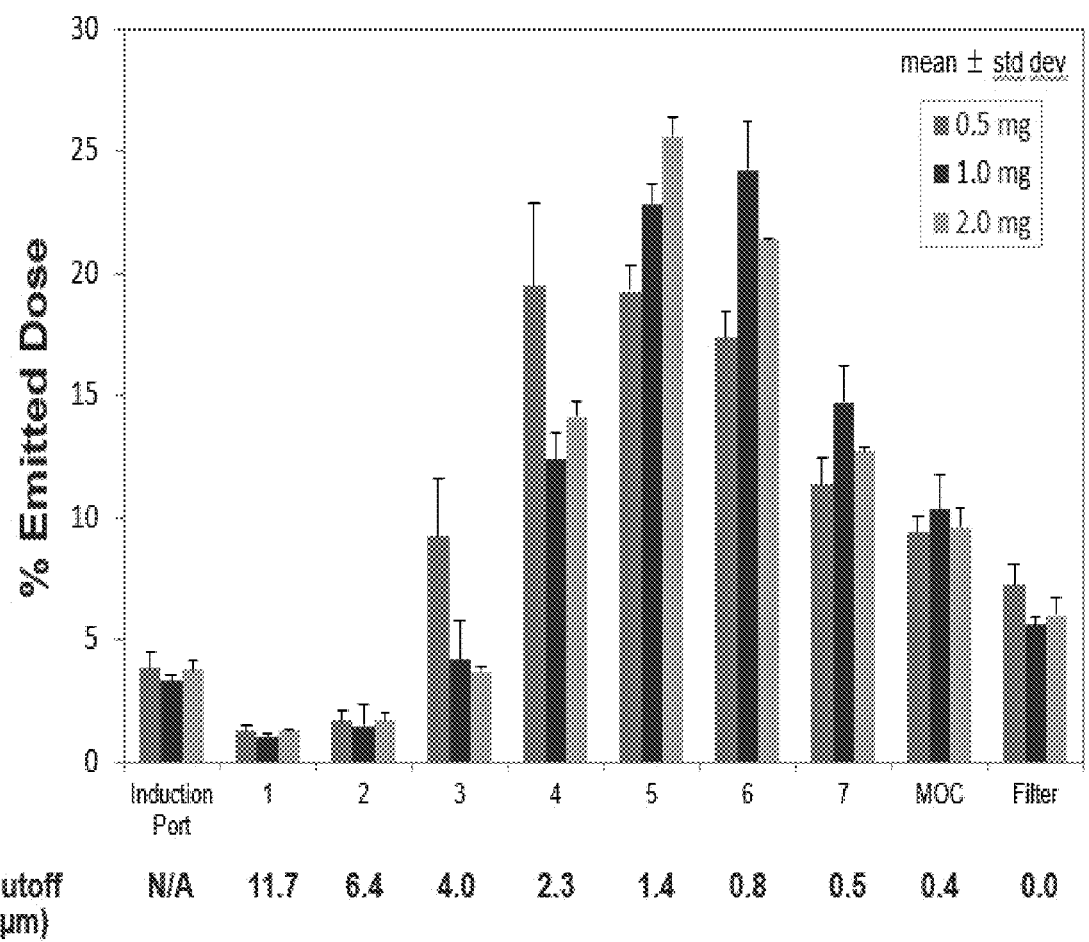

As shown in FIG. 4, the particle size distribution of the alprazolam aerosol in one embodiment has alprazolam particles having a MMAD of 1.2 to 1.8 microns. At least 80% by weight of the alprazolam aerosol particles have a size less than 5 microns, preferably at least 90% by weight of the alprazolam aerosol particles have a size less than 5 microns. At least 50% by weight of the alprazolam aerosol particles have a size less than 2 microns, preferably at least 50% by weight of the alprazolam aerosol particles have a size less than 1 micron. The Next Generation Pharmaceutical Impactor (NGI) was used to determine the particle size distribution.

In some embodiments, the alprazolam is administered from a hand-held, single-dose, single-use inhalation device. The drug is administered in a single, normal breath, which is sufficient at typical patient tidal volumes to provide complete delivery of a dose of the alprazolam vapor. The single dose device may include a pull-tab that when pulled from the device renders it ready for use, which is indicated by illumination of a colored light located in the device housing. The device may remain active to facilitate delivery for a minimum of 15 minutes. To use, the patient simply exhales and then seals his or her lips around the mouthpiece of the product and inhales deeply, leading to generation and delivery of the drug aerosol. When the heat package is actuated, the green light turns off, indicating that the drug has been discharged. After use, the device is discarded. Since the heat package redox reaction occurs in an all-or-none fashion, the device contains no active reactants after use, nor can the product be reused.

The present invention delivers drugs non-invasively to the deep lung producing reliable IV-like pharmacokinetics. The breath-activated device delivers the drug while the patient simply takes a single inspiration through the mouthpiece without any other coordination needed. The drug delivery device and method for using it allows for self-administration and high reliability of delivery, producing rapid drug delivery and faster onset of action. Delivery of alprazolam in accordance with the invention can provide clear advantages over routes of administration currently available or in development, i.e., rectal and nasal administration.

Studies conducted included safety pharmacology as well as acute and repeat-dose toxicity studies in dogs and rats. Aerosolized alprazolam was used in these studies as it is the intended route of administration in clinical trials. The lone exception (as noted below) was the use of intravenous (IV) bolus administration in the safety pharmacology study. Safety studies are summarized briefly below.

In a pharmacokinetic (PK) study in dogs, alprazolam PK was profiled following either intravenous or inhalation administration. Mean bioavailability was estimated to be 85-96% with an inhalation $T_{max}$ of less than 1 minute.

In a 5-day exploratory inhalation toxicity study in dogs, the no-observed-adverse-effect level was 1.5 mg/kg/day for treatment-related histopathological findings.

In a 28-day GLP inhalation toxicity study with a 14-day recovery period in dogs, the no-observed-effect level for the histopathological finds was 2.8 and 4.4 mg/kg/day for males and females, respectively. There were no deaths during the course of the study. The immunogenic potential of alprazolam was assessed and there were no immunoglobulin or hypersensitivity response.

In a cardiovascular and respiratory safety study in dogs intravenously dosed with alprazolam over 5 sec, a transient decrease in respiratory rate and transient increase in heart rate were found. However, these changes were within normal ranges and not considered biologically significant. The plasma concentration of alprazolam associated with modest cardiovascular or respiratory effects exceeded 900 ng/mL and would not be expected to induce any significant changes at the range of doses planned considered for clinical studies (0.5 to 2.0 mg).

In a rat inhalation MTD study, a single dose of inhaled alprazolam was well tolerated up to 10.8 mg/kg and did not result in any adverse signs of toxicity. In the 14-day inhalation toxicity study in rats, the no-adverse-effect level was considered to be 10.3 mg/kg/day.

In vitro drug transporter and cytochrome P450 inhibition potential were also studied. No inhibition was observed at the maximum alprazolam concentration tested.

A Phase 2a proof-of concept study to investigate the potential of inhaled alprazolam in patients with photosensitive epilepsy was recently completed (See Example 1).

Oral inhalation treatment using inhaled alprazolam will focus on subtypes of patients diagnosed with partial onset (focal) or generalized seizure disorder in which acute treatment with a benzodiazepine for a rapid anti-seizure activity could be beneficial. Inhaled alprazolam has been shown to produce a rapid rise in alprazolam plasma levels (less than 2 min) and effects on EEG in patients with photosensitive epilepsy within 2 minutes. Patient subtypes under consideration include patients with cluster seizures; patients with seizure events that include a predictable prodrome, aura, or evolution of their seizures, such that a change in that pattern of evolution can be detected; and patients with juvenile myoclonic epilepsy.

Because epilepsy is commonly found in individuals under the age of 18, adolescent patients represent a significant subpopulation that might benefit from inhaled alprazolam. Efficacy and tolerability data from adults, such as age 18-60, or older, can be informative for dose selection in the younger population. Studies on adolescent subjects (ages 13-17) assessing PK, safety and tolerability prior to Phase 3 could be used to inform the doses for this age range. Modeling and simulation of clinical study data in adults and adolescents may be used to support the dose selection for those age groups and may also inform dose selection for children less than 13 years old.

Other indications where the invention may be used include acute panic attack, severe dental anxiety, post-traumatic stress disorder (PTSD), autism with intermittent aggressive behavior, or for certain ophthalmic procedures.

EXAMPLES

The following examples are provided for illustrative purposes only and are not intended to limit the scope of the invention.

Example 1 evaluated the ability of inhaled alprazolam to rapidly suppress photosensitivity in a double blind placebo-controlled crossover proof of concept study. This study was an in-clinic, randomized, placebo-controlled, double-blind design, 5-way crossover study design, which allowed for small patient size. Epilepsy patients were evaluated using an Intermittent Photic Stimulation model, allowing for screening for antiepileptic effects without triggering seizures or convulsive responses. Three doses of alprazolam were investigated along with placebo (twice) in 5 subjects.

In patients with photosensitive epilepsy, intermittent photic stimulation was used to elicit generalized epileptiform EEG activity. The subject is exposed to certain frequency of light stimulation (flash frequencies), and photosensitivity range measured. The model has been used to identify antiepileptic effects on a number of drugs. The model is specific (sedative drugs did not show photosensitivity).

The primary objectives of the study were to assess 1) the effects of inhaled alprazolam on the IPS-induced photoparoxysmal EEG response in patients with epilepsy, 2) the sedative properties of these doses in order to select maximally-effective dose with the least sedation for further clinical studies, and 3) overall safety. The primary endpoint was the change in the Standard Photosensitivity Range (SPR) in subjects receiving each dose of inhaled alprazolam.

Patients at least 18 years old with photosensitive epilepsy at 3 sites were tested on a baseline day, and then received in randomized order either inhaled placebo (on 2 days) or 0.5, 1 or 2 mg inhaled alprazolam delivered using a hand-held inhaled alprazolam device. Study days were separated by at least 1 week. Presence (and degree) of photosensitivity was measured predose, then at 2 min, 10 min, 30 min, 1, 2, 4 and 6 hours post-dose. Plasma concentration of study drug was measured at each time point. Sedation was assessed at each time point using the 100-mm linear visual analogue scale (VAS).

The test subjects were exposed to intermittent photic stimulation (14 frequencies, from 2 to 60 Hz), starting with lowest frequency and increasing frequency stepwise until a photosensitivity response was elicited. The test was repeated with the highest frequency and decreased frequency. The results can be summarized in a quantitative measure known as the Standardized Photosensitive Range (SPR). The Maximum SPR is 14. In the example shown, SPR is 8. The Primary endpoint is reduction in mean SPR, which is an indication of antiseizure activity. Patients that have a relatively stable SPR were enrolled in the study to allow for small study size.

Secondary study endpoints included assessment of sedation using two visual analogue scales (VAS); correlation of plasma concentrations of inhaled alprazolam with PD effects on the SPR range; correlation of plasma concentrations of inhaled alprazolam with PD effects on sedation; and assessment of adverse events and changes in the neurological examination.

Five patients were enrolled and completed all treatment arms. All doses decreased the mean standardized photosensitivity range (SPR), with maximal or near-maximal effect occurring by 2 minutes post dose. Higher doses produced effects on SPR out to 4 hours. Sedation was dose related, but separated from SPR effects at later time points. Treatment was well tolerated with no serious adverse events.

The effects of inhaled alprazolam were assessed on the IPS-induced photoparoxysmal EEG response in patients with epilepsy. The plasma concentrations of inhaled alprazolam were correlated with pharmacodynamic effects on IPS and sedation (PK/PD correlation). The sedative properties of these doses were assessed in order to select maximally effective dose with the least sedation for further clinical studies. The safety of a single dose of inhaled alprazolam was assessed in patients with photosensitive epilepsy.

Figure 5A:
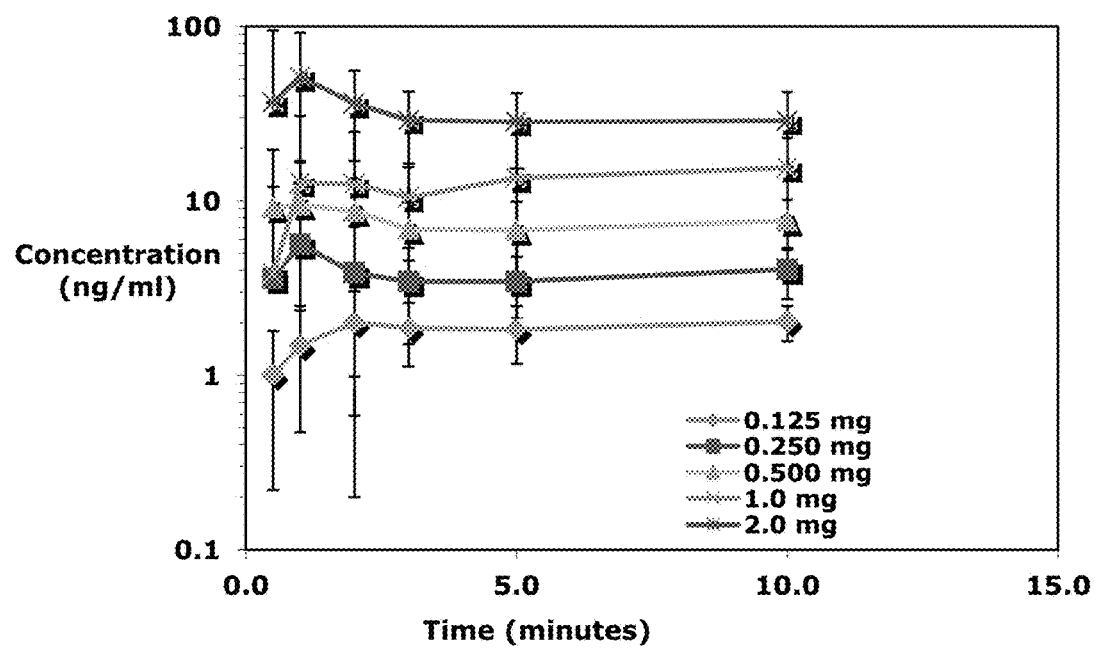
Figure 5B:
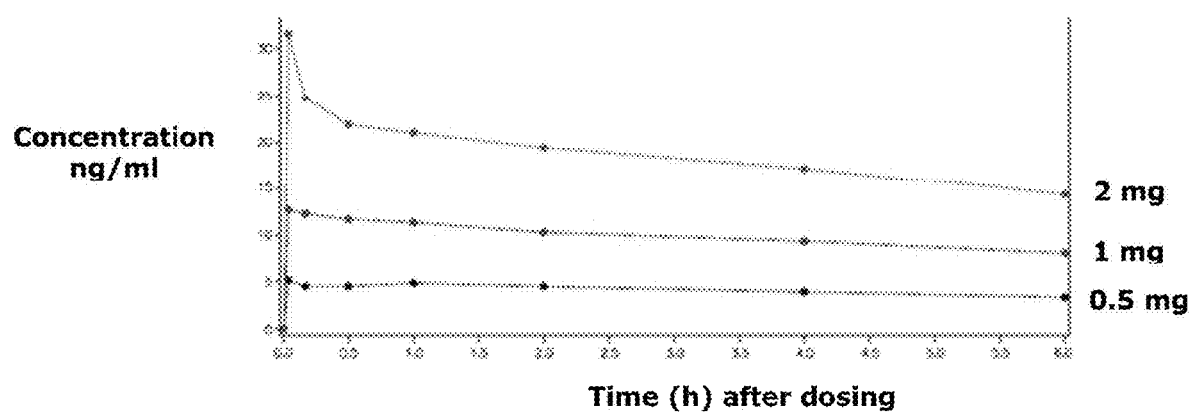

FIGS. 5A and 5B show graphs of the mean plasma concentration of alprazolam in phase 1 and phase 2a clinical trials respectively. The graphs indicate a rapid uptake of alprazolam into the plasma after oral administration of the condensation aerosol. Notably, oral administration as described herein provides plasma uptake of alprazolam wherein the $T_{max}$ is less than 15 minutes post administration, or wherein the $T_{max}$ is less than 5 minutes post administration or wherein the $T_{max}$ is less than 2 minutes post administration. Mean peak plasma concentration occurred one to two minutes after administration of the alprazolam concentration aerosol. Delivery of the alprazolam via inhalation of a condensation aerosol resulted in a $C_{max}$ of at least 5 ng/ml, or at least 12 ng/ml or at least 30 ng/ml less than 5 minutes after administration, when administered in doses of at least 0.5 mg.

The change in the SPR range in subjects receiving each dose of inhaled alprazolam was compared to placebo. A correlation of plasma concentrations of inhaled alprazolam with pharmacodynamic effects on the SPR range was made. FIG. 6 shows a graph of the mean standardized photosensitivity rage (SPR) over time for the three dose rates used in the study. All three inhaled alprazolam doses produced a decrease in mean SPR (primary study endpoint). For all doses, maximal or near-maximal effect occurred by about 2 minutes. The maximal decrease in epileptic response compared to placebo for all three doses at two minutes suggest rapid anti-epileptic activity.

With respect to the magnitude of the change in SPR, a maximal decrease of approximately 5 steps was obtained, at least at the earlier time points. For the 1 mg and 2 mg doses, almost complete elimination of the photosensitivity was achieved. These effects represent meaningful changes. For example, the 90% Confidence Interval was determined for the mean change in SPR from baseline for each dose at each time point. Magnitude and duration of effect was comparable for 1 mg and 2 mg. The results at the first time point (2 minutes) is illustrated where there is no or minimal overlap in the Confidence Interval.

The results demonstrated a maximal or near-maximal decrease in epileptiform response (primary endpoint) for all doses (0.5 mg, 1 mg and 2 mg) by the 2 minute timepoint, suggesting rapid anti-epileptic activity.

FIGS. 7A and 7B show EEG traces of a representative patient prior to and after dosing with alprazolam condensation aerosol respectively. The post-dose traces show complete abolishment of epileptiform activity. The epileptiform activity shown in FIG. 7A shows erratic brain activity during a seizure. After treatment the brain activity reverts to normal as seen in FIG. 7B.

Figure 8:
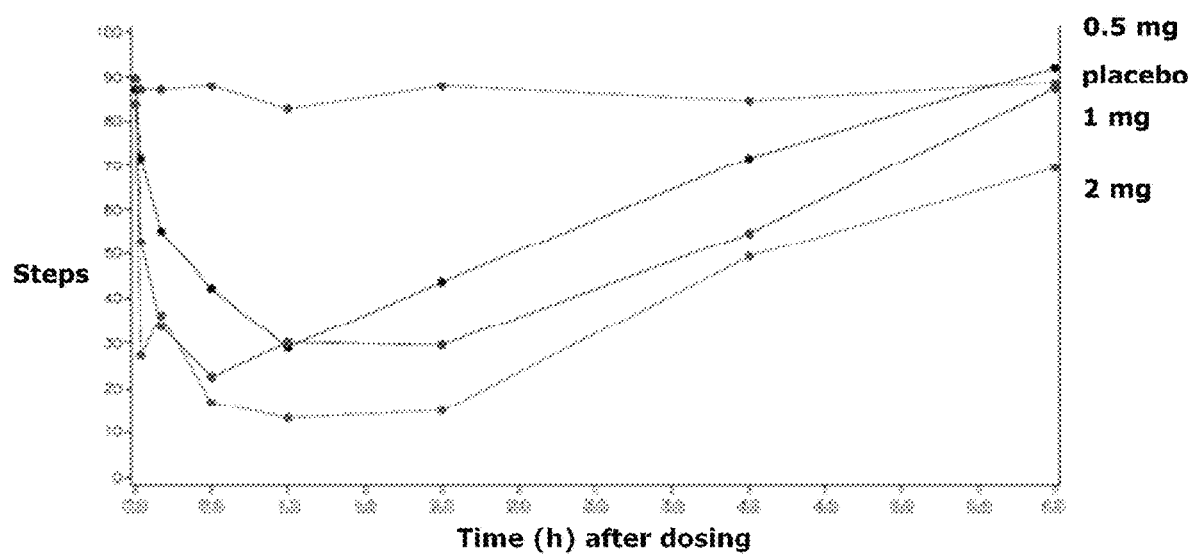

Assessment of the sedation using 2 visual analogue scales was made. FIG. 8 shows a graph of the mean Visual Analogue Scale (VAS) for patients after dosing with alprazolam condensation aerosol. A correlation of plasma concentrations of inhaled alprazolam with pharmacodynamic effects on sedation was made. VAS measures sedation and suggests rapid onset of action in the brain after oral inhalation administration of alprazolam. Maximum sedation occurred within about two minutes of administration of alprazolam. Clinical observations support early onset of sedation at 30 seconds.

Correlation between the SPR and VAS responses showed that both responses showed onset in less than two minutes, demonstrating a rapid, predictable onset of effect. Sedation recovered to near placebo levels within six hours of administration. Reduction of SPR was generally maintained for at least six hours after administration, demonstrating an adequate duration of effect, without being too long. A 1 mg dose may be optimal for balancing potential anti-epileptic effect with the level of sedation.

An assessment of adverse events and changes in the neurological examination were made. The safety profile was consistent with oral alprazolam. No significant treatment emergent adverse events were observed, as summarized in Table 1. The minimal adverse effects suggest that the treatment was well tolerated.

TABLE 1

| Adverse Event | Placebo N = 5, n | 0.5 mg N = 5, n | 1 mg N = 5, n | Total number of subjects experiencing an event |
|---|---|---|---|---|
| Cough | 0 | 2 | 1 | 2 |
| Dizziness | 0 | 1 | 0 | 1 |
| Dysgeusia | 1 | 2 | 2 | 2 |
| Oral Dysaesthesia | 0 | 2 | 0 | 2 |
| Sedation/ somnolence | 1 | 1 | 2 | 2 |

Bioavailability can be determined by a suitable pharmacodynamics method, such as comparison of area under the blood plasma concentration curve (AUC) for the inhaled and intravenously administered drug. It is further understood that the percent bioavailability of the inhalation administered alprazolam may be determined by comparing the area under the blood plasma concentration curve obtained with one dose of the alprazolam (e.g. 1 mg of inhaled alprazolam) with another dose of alprazolam administered intravenously (e.g. 0.5 mg of i.v. alprazolam), taking into consideration the difference in dose. Thus, for the sake of illustration, a 1 mg inhaled alprazolam dose that achieves an AUC that is precisely half of the AUC obtained with 0.5 mg of i.v. alprazolam would have a bioavailability of 100%.

In summary, all three inhaled alprazolam doses produced a decrease in mean SPR (primary study endpoint). For all doses, maximal or near-maximal effect occurred by 2 minutes. Magnitude and duration of effect was comparable for 1 mg and 2 mg. Dose related changes were observed in the visual-analogue scale (VAS) for sedation and sleepiness, importants marker for potential adverse events associated with dosing. PK analysis showed dose proportionality with plasma concentrations. In all cases, treatment with the inhaled drug was generally well tolerated, with no reported serious adverse events (SAEs) at doses up to 2 mg. Expected CNS adverse events (primarily sedation and somnolence) showed that respiratory AEs were mild or moderate and were resolved. The effect on SPR shows rapid anti-epileptic activity.

In conclusion, the results from this study demonstrated rapid and substantive decrease in mean SPR at all three inhaled alprazolam doses. For all doses, maximal or near-maximal effect occurred by the 2 minute timepoint. The magnitude and duration of the effect was comparable for the 1 mg and 2 mg doses. Dose related changes were observed in the visual-analogue scale (VAS) for sedation and sleepiness, but over a different time frame than the observed changes in SPR. Overall, the decrease in SPR suggests the potential for rapid anti-epileptic activity.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

The invention claimed is:

1. A method for stopping an ongoing seizure in a subject in need thereof,
the method comprising administering alprazolam via a breath-activated inhalation device during the ongoing seizure which has not progressed to status epilepticus, wherein the alprazolam is administered in a dose of about 1 mg to about 2 mg, wherein the inhalation device comprises:
a first element for rapidly heating a heat-conductive, impermeable substrate coated with an alprazolam composition to form a vapor;
a second element allowing the vapor to cool, thereby providing a condensation aerosol comprising alprazolam particles, and
a third element permitting inhalation of the condensation aerosol;
and
whereby the ongoing seizure is stopped within 2 minutes of inhalation of alprazolam.

2. The method of claim 1, wherein said subject is an epilepsy patient having an aura, a focal seizure that is expected to secondarily generalize, or is a patient with juvenile myoclonic epilepsy wherein a seizure typically manifests over a period of minutes.

3. The method of claim 1, wherein the ongoing seizure is a prolonged focal seizure.

4. The method of claim 1, wherein the subject is an epilepsy patient and the ongoing seizure is selected from absence seizures and myoclonic seizures.

5. The method of claim 1, wherein the subject is an epilepsy patient and the ongoing seizure is in the aura phase.

6. The method of claim 1, wherein the subject is an epilepsy patient and the ongoing seizure is a prolonged focal seizure or a myoclonic seizure which typically manifests over a period of minutes.

7. The method of claim 1, wherein the alprazolam exhibits alprazolam plasma Tmax of less than 5 minutes post administration.

8. The method of claim 1, wherein the alprazolam exhibits alprazolam plasma Tmax of less than 2 minutes post administration.

9. The method of claim 1, wherein the alprazolam has maximal or near maximal therapeutic effect within 2 minutes after administering.

10. The method of claim 1, wherein the alprazolam is administered in a dose of between 1 mg and 2 mg.

11. The method of claim 1, wherein the alprazolam is administered in a dose of 2 mg.

12. The method of claim 11, wherein said subject is an epilepsy patient with an aura, cluster (acute repetitive) seizures, prolonged focal (partial) seizures, or juvenile myoclonic epilepsy.

13. The method of claim 11, wherein the subject is an epilepsy patient and the ongoing seizure is a prolonged focal seizure or a myoclonic seizure.

14. The method of claim 11, wherein the alprazolam is administered a single inspiration without any other coordination needed.

15. The method of claim 1, wherein the method achieves bioavailability that is from about 80 to 125% of that achieved with alprazolam administered intravenously.

16. The method of claim 1, wherein at least 80% by weight of the alprazolam particles have a size less than 5 micron.

17. The method of claim 1, wherein at least 90% by weight of the alprazolam particles have a size less than 5 micron.

18. The method of claim 1, wherein at least 50% by weight of the alprazolam particles have a size less than 2 micron.

19. The method of claim 1, wherein the condensation aerosol is substantially excipient free.

20. The method of claim 1, wherein the condensation aerosol is excipient free.

21. The method of claim 1 wherein the alprazolam is self-administered after onset of the ongoing seizures.

22. The method of claim 1, wherein the subject has no impairment of consciousness or awareness during the ongoing seizure.

23. The method of claim 1, wherein the condensation aerosol is provided by preparing an alprazolam film of a thickness of between 0.05 and 20 microns on a heat-conductive and impermeable substrate and heating said substrate to at least 300° C. to vaporize the alprazolam.

24. The method of claim 23, wherein the alprazolam film has a thickness of between 0.1 and 10 microns, and wherein the alprazolam composition is heated to 390° C.±50° C.

25. The method of claim 23, wherein alprazolam is administered in a dose of about 2 mg.

26. The method of claim 1, wherein the alprazolam composition is provided as a film having a thickness of between 0.1 and 10 microns,
wherein the heating comprises heating to 390° C.±50° C., and
wherein at least 80% by weight of the alprazolam particles have a size of less than 5 µm.

27. The method of claim 26, wherein alprazolam is administered in a dose of 2 mg.

28. The method of claim 26, wherein the inhalation device is a single-use, disposable inhaler.

29. The method of claim 26, wherein said subject is an epilepsy patient and the ongoing seizure is selected from prolonged focal seizures, absence seizures, and myoclonic seizures.

30. The method of claim 29, wherein alprazolam is administered in a single normal breath.

31. The method of claim 29, wherein alprazolam is self-administered in a dose of about 2 mg.

32. The method of claim 26, wherein a gas flow rate over the alprazolam composition during heating is between about 4 and 50 L/minute, wherein the alprazolam composition is provided as a film having a thickness of between 1 and 5 microns and wherein at least 50% by weight of the alprazolam particles have a size less than 2 micron.

33. The method of claim 1, wherein the subject is an epilepsy patient with cluster (acute repetitive) seizures.

34. The method of claim 1, wherein the alprazolam is administered in a single, normal breath.

* * * * *